(12) United States Patent
Natarajan et al.

(10) Patent No.: US 6,638,208 B1
(45) Date of Patent: Oct. 28, 2003

(54) INTRAURETHRAL CONTINENT PROTHESIS

(75) Inventors: Ananth Natarajan, New Port Richey, FL (US); Nitish V. Thakor, Clarksville, MD (US)

(73) Assignee: Infinite Biomedical Technologies, LLC, Baltimore, MD (US)

( * ) Notice: Subject to any disclaimer, the term of this patent is extended or adjusted under 35 U.S.C. 154(b) by 0 days.

(21) Appl. No.: 09/391,077

(22) Filed: Sep. 4, 1999

Related U.S. Application Data

(60) Provisional application No. 60/100,396, filed on Sep. 15, 1998.

(51) Int. Cl.$^7$ ................................................. A61B 5/00

(52) U.S. Cl. .......................................................... 600/30

(58) Field of Search .............. 600/29–31; 128/DIG. 25, 128/885

(56) References Cited

U.S. PATENT DOCUMENTS

| | | | |
|---|---|---|---|
| 3,750,194 A | * 8/1973 | Summers | 600/30 |
| 4,399,809 A | 8/1983 | Baro et al. | |
| 4,681,572 A | 7/1987 | Tokarz et al. | |
| 4,850,963 A | 7/1989 | Sparks et al. | 600/29 |
| 4,961,725 A | * 10/1990 | Rey et al. | 128/DIG. 25 |
| 5,140,999 A | 8/1992 | Ardito | |
| 5,476,434 A | * 12/1995 | Kalb et al. | 600/30 |
| 5,609,559 A | 3/1997 | Weitzner | 600/29 |
| 5,704,353 A | * 1/1998 | Kalb et al. | 128/903 |
| 5,704,893 A | 1/1998 | Timm | 600/29 |
| 5,997,467 A | 12/1999 | Connolly | |
| 6,056,687 A | 5/2000 | Polyak et al. | |
| 6,067,991 A | * 5/2000 | Forsell | 600/30 X |
| 6,119,697 A | 9/2000 | Engel et al. | |
| 6,135,945 A | * 10/2000 | Sultan | 600/30 |

OTHER PUBLICATIONS

PCT International Search Report for application No. PCT/US99/20377, date of mailing Dec. 23, 1999.

PCT International Preliminary Examination Report for application No. PCT/US99/20377, date of mailing Apr. 27, 2001.

Cruise et al., "Epidemiology of Urinary Incontinence in Older Adults," Chapter 5 in *Urogynecology and Urodynamics Theory and Practice*, Ostergard, Ed., at 76–79 (1996).

Burgio et al., "Treatment Seeking for Urinary Incontinence in Older Adults," *JAGS*, vol. 42, No. 2 at 208–212 (Jan. 1994).

Sandvik et al., "Validation of a Severity Index in Female Urinary Incontinence and its Implementation in an Epidemiological Survey," *J. Epidemiology & Community Health*, vol. 47 at 497–499 (1993).

Milsom et al., "The Influence of Age, Parity, Oral Contraception, Hysterectomy and Menopause on the Prevalence of Urinary Incontinence in Women," *J. Urology*, vol. 149 at 1459–1462 (Jun. 1993).

Hunskaar et al., "The Quality of Life in Women with Urinary Incontinence as Measured by the Sickness Impact Profile," *JAGS*, vol. 39, No. 4, at 378–382 (Apr. 1991).

(List continued on next page.)

Primary Examiner—Samuel G. Gilbert
(74) Attorney, Agent, or Firm—Konrad Raynes Victor & Mann, LLP; Alan S. Raynes

(57) ABSTRACT

An implantable apparatus may include a plug member having a lumen and a valve adapted to open and close the lumen in response to a signal. The apparatus may also include at least one sensor and a controller adapted to control the valve. The controller may be programmable to open the valve to permit the flow of urine under at least one mode of operation selected from a predetermined time interval operation, a sensor operation, and a manual actuation operation.

41 Claims, 6 Drawing Sheets

OTHER PUBLICATIONS

Shiga et al., "Electrically Driven Polymer Gel Finger Working in the Air," *J. Intelligent Mat'l. Systems & Structures*, vol. 4 at 553–557 (Oct. 1993).

Rossi et al., "Pseudomuscular Gel Actuators for Advanced Robotics," *J. Intelligent Mat'l. Systems & Structures*, vol. 3 at 75–95 (Jan. 1992).

Wagner et al., "Quality of Life of Persons With Urinary Incontinence: Development of a New Measure," *Adult Urology*, vol. 47, No. 1 at 67–72 (1996).

Wagner et al., "Economic Costs of Urinary Incontinence in 1995," *Urology*, vol. 51, No. 3 at 355–361 (1998).

Burch, "Urethrovaginal Fixation to Cooper's Ligament for Correction of Stress Incontinence, Cystocele, and Prolapse," *Am, J. Obstet. and Gynecol.*, vol. 81, No. 2 at 281–290 (Feb. 1961).

van Geelen et al., "The Clinical and Urodynamic Effects of Anterior Vaginal Repair and Burch Colposuspension," *Am. J. Obstet. Gynecol.*, vol. 159, No. 1 at 137–144 (Jul. 1988).

Stanton et al., "A Comparison of Vagina and Suprapubic Surgery in the Correction of Incontinence Due to Urethral Sphincter Incompetence," *British Journal of Urology*, vol. 51 at 497–499 (1979).

Vierhout et al., "De Novo Detrusor Instability After Burch Colposuspension," *Acta Obstet Gynecol Scand*, vol. 71 at 414–416 (1992).

DeLancey, "Structural Support of the Urethra as It Relates to Stress Urinary Incontinence: The Hammock Hypothesis," *American Journal of Obstetrics and Gynecology*, vol. 170, No. 6 at 1713–1723 (Jun. 1994).

Doggweiler et al., "Sling Surgery and Bladder Instability; An Animal Model," *The Journal of Urology*, vol. 161(4S) at 309 (Apr. 1999).

Shiga et al., "Bending of Poly (Vinyl Alcohol)–Poly (Sodium Acrylate) Composite in Electric Fields," *Journal of Applied Polymer Science*, vol. 44 at 249–253 (1992).

Sawahata et al., "Electrically Controlled Drug Delivery System Using Polyelectrolyte Gels," *Journal of Controlled Release*, vol. 14 at 253–262 (1990).

Caldwell, "Natural and Artificial Muscle Elements as Robot Actuators," *Mechatronics*, vol. 3, No. 3 at 269–283 (1993).

Wiskind et al., "The Incidence of Genital Prolapse After the Burch Colposuspension," *Am. J. Obstet. Gynecol.*, vol. 167, No. 2 at 399–405 (1992).

Lim et al., "The Abrams–Griffiths Nomogram," *World Journal of Urology*, vol. 13 at 34–39 (1995).

Kishi et al., "Mechanism and Process of Chemomechanical Contraction of Polyelectrolyte Gels Under Electric Field," *Polymers for Advanced Technologies*, vol. 1 at 19–25 (1990).

Cardozo et al., "Genuine Stress Incontinence and Detrusor Instability–A Review of 200 Patients," *British J Obstetrics and Gynaecology*, vol. 87 at 184–190 (Mar. 2000).

Kelleher et al., "The Impact of Urinary Incontinence on Sexual Function," *Sexual Health*, vol. 3 at 186–191 (1994).

Koyano et al., "Prevalence and Outcome of Low ADL and Incontinence Among the Elderly: Five Years Follow–up in a Japanese Urban Community," *Arch. Gerontol. Geriatr.*, vol. 5 at 197–206 (1986).

Laird et al., "Random–Effects Models for Longitudinal Data," *Biometrics*, vol. 38 at 963–974 (Dec. 1982).

Bergman et al., "Role of the Q–tip Test in Evaluating Stress Urinary Incontinence," *The Journal of Reproductive Medicine*, vol. 32, No. 4 at 273–275 (Apr. 1987).

Sirls et al., "The Effect of Study Methodology on Reported Success Rates of the Modified Pereyra Bladder Neck Suspension," *The Journal of Urology*, vol. 154 at 1732–1735 (Nov. 1995).

Klutke et al., "Urodynamic Changes in Voiding After Anti–Incontinence Surgery: An Insight into the Mechanism of Cure," *Urology*, vol. 54, No. 6 at 1003–1007 (Dec. 1999).

Marshall et al., "The Correction of Stress Incontinence By Simple Vesicourethral Suspension," *Surgery, Gynecology, and Obstetrics*, vol. 88 at 509–518 (1949).

Schmidt, "Advances in Genitourinary Neurostimulation," *Neurosurgery*, vol. 18, No. 6 at 1041–1044 (1986).

McGuire et al., "Stress Urinary Incontinence," *Journal of Obstetrics and Gynecology*, vol. 47, No. 3 at 255–264 (1976).

Cupples et al., "Comparison of Baseline and Repeated Measure Covariate Techniques in the Framingham Heart Study," *Statistics in Medicine*, vol. 7 at 205–218 (1988).

Hording et al., "Urinary Incontinence in 45–Year–Old Women An Epidemiological Survey," *Scand J Urol Nephrol*, vol. 20 at 183–186 (1986).

Schmidt, "Applications of Neurostimulation in Urology," *Neurourology and Urodynamics*, vol. 7 at 585–592 (1988).

Abrams et at., "Standardisation of Terminology of Lower Urinary Tract Function," *Neurourology and Urodynamics*, vol. 7 at 403–427 (1988).

Bhattacharyya et al., "On the Role of Thermoelectric Heat Transfer in the Despign of SMA Actuators: Theoretical Modeling and Experiment," *Smart Mater. Struct.*, vol. 4 at 252–263 (1995).

Alcalay et al., "Burch Colposuspension: A 10–20 year Follow Up," *British Journal of Obstetrics and Gynecology*, vol. 102 at 740–745 (Sep., 1995).

Hamlen et al., "Electrolytically Activated Contractile Polymer," *Nature*, vol. 206 at 1149–1150 (Jun. 12, 1965).

Suzuki et al., An Artificial Muscle of Polyvinyl Alcohol Hydrogel Composites, Abstract of paper from *Biorheology*, vol. 23 at 874–878 (1986).

Schetky, "Shape–Memory Alloys," *Scientific American*, vol. 24 at 74–82 (1979).

Henriksson et al., "A Urodynamic Evaluation of the Effects of Abdominal Urethrocystopexy and Vaginal Sling Urethroplasty in Women With Stress Incontinence," *American J. Obstet. Gynecology* vol. 131, No. 1 at 77–82 (1978).

Webster et al., "Voiding Dysfunction Following Cystourethropexy: Its Evaluation and Management," *The Journal of Urology*, vol. 144 at 670–673 (Sep. 1990).

Zaragoza, "Expanded Indications For the Pubovaginal Sling: Treatment of Type 2 or 3 Stress Incontinence." *The Journal of Urology*, vol. 156 at 1620–1622 (Nov. 1996).

Mainprize et al., "The Marshall–Marchetti–Krantz Procedure: A Critical Review," *Obstetrical and Gynecology Survey*, vol. 43, No. 12 at 724–729 (1988).

Hayashi et al., "Development of Piezoelectric Cycloid Motor," 2/1 to 2/3, paper published in English in *Mechatronics* (1991).

Iosif et al., "Estrogen Receptors in the Human Femal Lower Urinary Tract," *Am. J. Obstet. Gynecol.*, vol. 141, No. 7 at 817–820 (1981).

Raz et al., "The Raz Bladder Neck Suspension: Results in 206 Patients" *Urological Neurology and Urodynamics*, vol. 148 at 845–850 (1992).

Karram et al., "The Modified Pereyra Procedure: A Clinical and Urodynamic Review," *British Journal of Obstetrics and Gynecology*, vol. 99 at 655–658 (Aug. 1992).

Hilton, "A Clinical and Urodynamic Study Comparing the Stamey Bladder Neck Suspension and Suburethral Sling Procedures in the Treatment of Genuine Stress Incontinence," *British Journal of Obstetrics and Gynecology*, vol. 96 at 213–220 (Feb. 1989).

Bergman et al., "Three Surgical Procedures for Genuine Stress Incontinence: Five–year Follow–up of a Prospective Randomized Study," *American Journal of Obstetrics and Gynecology*, vol. 173, No. 1 at 66–71 (Jul. 1995).

Beck et al., "A 25–Year Experience With 519 Anterior Colporrhaphy Procedures," *Obstetrics and Gynecology*, vol. 78, No. 6 at 1011–1018 (Dec. 1991).

Rubinstein et al., "Elastic Modulus and Equilibrium Swelling of Polyelectrolyte Gels," *Macromolecules*, vol. 29, No. 1 at 398–406 (1996).

Kelly et al., "Urinary Incontinence in Women, Without Manifest Injury to the Bladder," *Surgery, Gynecology and Obstetrics*, vol. 18 at 444–450 (1914).

Ou et al., "Laparoscopic Bladder Neck Suspension Using Hernia Mesh and Surgical Staples," *Journal of Laparoendoscopic Surgery*, vol. 3, No. 6 at 563–566 (1993).

Goldstein et al., "Urinary Incontinence Why People Do Not Seek Help," *Journal of Gerontological Nursing*, vol. 18 at 15–20 (Apr. 1992).

Grimby et al., "The Influence of Urinary Incontinence on the Quality of Life of Elderly Women," *Age and Ageing*, vol. 22 at 82–89 (1993).

Wagner et al., "Economic Costs of Urinary Incontinence in 1995," *Urology*, vol. 51, No. 3, at 355–361 (1998).

Molander et al., "An Epidemiological Study of Urinary Incontinence and Related Urogenital Symptoms in Elderly Women," *Maturitas*, vol. 12 at 51–60 (1990).

Wyman et al., "Psychosocial Impact of Urinary Incontinence in the Community–Dwelling Population," *JAGS*, vol. 38, No. 3 at 282–288 (Mar. 1990).

Colombo et al., "Gynecology: Burch Colposuspension Versus Modified Marshall–Marchetti–Krantz Urethropexy for Primary Genuine Stress Urinary Incontinence: A Prospective, Randomized Clinical Trial," *American Journal of Obstetrics and Gynecology*, vol. 171, No. 6 at 1573–1579 (Dec. 1994).

Jensen et al., "The Role of Patient History in the Diagnosis of Urinary Incontinence," *Obstetrics and Gynecology*, vol. 83, No. 5, Part 2 at 904–910 (1994).

Enzelsberger et al., "Comparison of Burch and Lyodura Sling Procedures for Repair of Unsuccessful Incontinence Surgery," *Obstet Gynecol*, vol. 88, No. 2 at 251–256 (Aug. 1996).

Pereyra, "A Simplified Surgical Procedure for the Correction of Stress Incontinence in Women," *West. J. Surg. Obst. and Gynec.* 223–226 (Jul.–Aug. 1959).

Klutke et al., "Bladder Neck Suspension for Stress Urinary Incontinence: How Does it Work?," *Neurourology and Urodynamics*, vol. 18 at 623–627 (1999).

Nambu, "A Rubber Like Polyvinyl Alcohol Gel," *Kobunshi Ronbunshu, (Japanese J. Polymer Sci Tech.)* vol. 47, No. 9 at 695–703 (Sep. 1990).

Klarskov et al., "Pelvic Floor Exercise Versus Surgery for Femal Urinary Stress Incontinence," *Urol. Int.*, vol. 41 129–132 (1986).

Oelrich, "The Striated Urogenital Sphincter Muscle in the Female," *The Anatomical Record*, vol. 205 at 223–232 (1983).

Bellouard et al., "A New Concept of Monolithic Shape Memory Alloy Micro–Devices Used in Micro–Robotics," *Actuator 98, $6^{th}$ International Conference on New Actuators*, Jun. 1998.

Sandvik et al., "Validation of a Severity Index in Female Urinary Incontinence and its Implementation in an Epidemiological Survey," *Journal of Epidemiology and Community Health*, vol. 47, at 497–499 (1993).

Sirls et al., "The Effect of Study of Methodology on Reported Success Rates of the Modified Pereyra Bladder Neck Suspension," *The Journal of Urology*, vol. 154 (1995).

Berkenblit et al., "Molecular electromechanics of cartilaginous tissues and polyelectrolyte gels," *Journal of Electrostatics*, vol. 34 at 307–330 (1995).

Osada et al., "Stimuli–Responsive Polymer Gels and Their Application to Chemomechanical Systems," *Prog. Polym. Sci.*, vol. 18 at 187–226 (1993).

Suzuki et al., "Electrostatic Effects and Counterion Condensation in Gels," *Springer Series in Synergetics, vol. 43, Cooperative Dynamics in Complex Physical Systems*, Ed. H. Takayama, Springer–Verlag, Berlin Heidelberg, at 76–77 (1989).

Liang et al., "Longitudinal data nanlysis using generalized linear models," *Biometrika*, vol. 73, No. 1 at 13–22 (1986).

Rogers, "Intelligent Materials," *Scientific American*, at 154–157 (Sep. 1995).

DeLancey, "Structural Support of the Urethra as it relates to stress urinary incontinence: The hammock hypothesis," *Am. J. Obstet. Gynecol*, vol. 170, No. 6 at 1713–1723 (Jun. 1994).

Wyman et al., "Psychosocial Impact of Urinary Incontinence in Women," *Obstetrics & Gynecology*, vol. 70, No. 3, Part I at 378–381 (Sep. 1987).

Cox, "Regression Models and Life–Tables," Read before the Royal Statistical Society, Mar. 8, 1972, pp. 187–220.

Takahashi, "Piezoelectric Actuators and Their Applications," *J. Inst. Elec. Info. Comm. Eng.*, vol. 70, No. 3 at 295–297 (1987).

Osada et al., "Electrically Activated Mechanochemical Devices Using Polyelectrolyte Gels," *Chemistry Letters*, at 1285–1288 (1985).

Koyano et al., "Prevalence and outcome of low ADL and incontinence among the elderly: five years follow–up in a Japanese urban community," *Arch. Gerontol. Geriatr.*, vol. 5 T 197–206 (1986).

Siegal, "Swelling Controlled Release from Hydrogels: An Evaluation of External Solute Effects," *Topics on Pharmaceutical Sciences 1993*, Ed. D.J.A. Crommelin, Int'l Pharmaceutical Federation, Stuttgard, Medpharm Scientific Publ., Chapter 31 at 459–468 (1994).

Smela et al., "Controlled Folding of Micrometer–Size Structures," Science, vol. 268 (Jun. 23, 1995) at 1735–1738.

Santa et al., "Characterization and modelling of a conducting polymer muscle–like linear actuator," *Smart Mater. Struct.* 6 (1997) at 23–24.

Smela et al., "Electrochemically Driven Polypyrole Bilayers for Moving and positioning Bulk Micromachined Silicon Plates," *Microelectromechanical Systems*, vol. 8, No. 4 (Dec. 1999) at 373–383.

Madden et al., "Fast contracting Polypyrrole actuators," *Synthetic metals*, 11312 (2000) at 185–192.

Jager et al., "Microfabricating Conjugated Polymer Actuators," *Science*, vol. 290 (Nov. 24, 2000) at 1540–1545.

\* cited by examiner

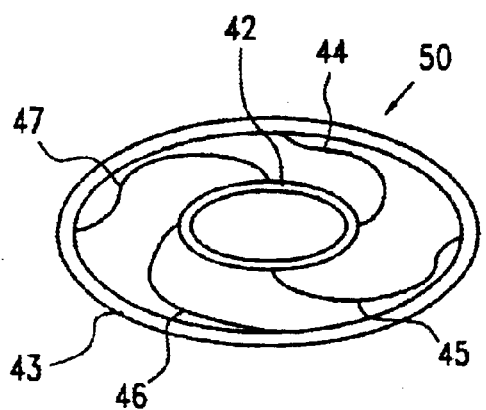
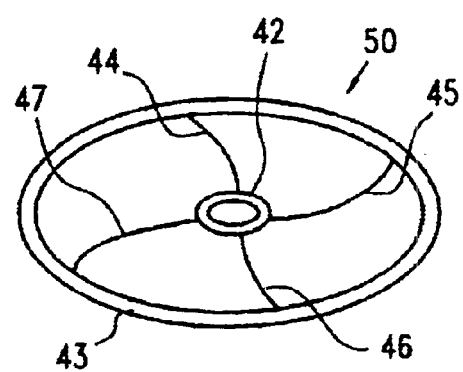
Fig. 5A        Fig. 5B
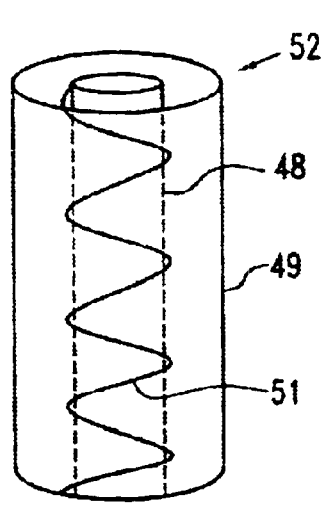
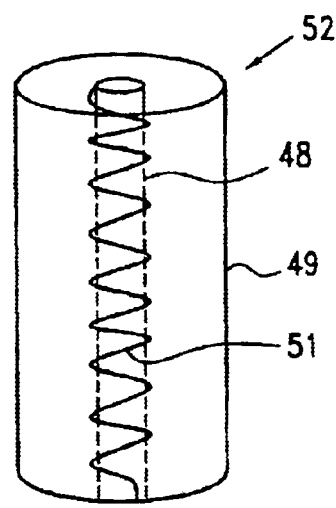
Fig. 6A        Fig. 6B

INTRAURETHRAL CONTINENT PROTHESIS

This application claims the benefit of U.S. Provisional Application No. 60/100,396, filed Sep. 15, 1998, entitled "Implanted Controllable Valve Apparatus."

FIELD OF INVENTION

The present invention relates to methods and apparatus for treatment of diseases and pathologies of the bladder, urinary sphincter or other sphincters.

BACKGROUND

Urinary incontinence affects 13 million American women. Incontinence is the involuntary loss of urine which is sufficient to impact the life style of the patient. Among community dwelling older adults, the reported incidence of incontinence is 3–25% with 15–36% complaining of severe incontinence. Further, these numbers are anticipated to rise substantially as the population ages. It is a major cause of deterioration of the quality of life and loss of independence. In fact, incontinence has been implicated as a major factor influencing individuals (and their families) to opt for admission into a nursing home, as they are no longer able to provide adequate care at home.

The predominant type of incontinence in women is genuine stress urinary incontinence (GSUI, which is implicated in 75–80% of cases). It is usually caused by a weakening of the pelvic floor muscles which is often associated with childbearing. This results in the displacement of the proximal urethra outside of the abdominal pressure zone. Therefore, an increase in intra-abdominal pressure is transmitted to the bladder but not to the urethra. The result is an involuntary loss of urine with cough, sneeze, or even with acts as simple as walking. Not surprisingly, a considerable amount of work has gone into development of a solution for this problem. Several treatments have been developed which aim to lift the bladder neck back into the abdomen. These procedures include the Burch urethropexy, the Kelly application, and the Marshall-Marchetti-Krantz suspension. The unfortunate downside to each of these is that they require surgical intervention and its associated morbidity. A minimally invasive, non-surgical therapy would be a significant improvement in the treatment of these patients.

SUMMARY OF THE INVENTION

One preferred embodiment of the present invention relates to an implantable apparatus including a plug member having a lumen and a valve adapted to open and close the lumen in response to a signal. The apparatus also includes at least one sensor and a controller adapted to control the valve.

In one aspect of certain Embodiments, the controller is programmable to open the valve to permit the flow of urine under at least one mode of operation selected from a predetermined time interval operation a sensor operation, and a manual actuation operation.

Another embodiment relates to a flow control apparatus for insertion into a patient's body, including an intravesicular pressure transducer and a polyelectrolytic hydrogel.

Another embodiment relates to a sphincter including an inner ring and an outer ring spaced a distance from the inner ring. The sphincter includes a plurality of hydrogel fibers extending between the inner ring and the outer ring.

Another embodiment relates to a sphincter having an inner tube and an outer tube surrounding the inner tube. The sphincter includes at least one hydrogel fiber wrapped around the inner tube. The hydrogel fiber is designed to contract in response to a signal and close the inner tube.

Yet another embodiment relates to an apparatus for controlling urine flow in a patient, including valve means for controlling the flow of urine. The valve means is implantable in the patient's body. The apparatus also includes a control means external to the patient's body for supplying a signal to control the valve means.

Another embodiment relates to an apparatus for controlling the flow of a substance in a patient's body. The apparatus includes an implantable valve placed at a position along the route that the substance flows through the body, and a controller for opening and closing the valve in response to an input provided by the patient.

Other embodiments relate to methods including a method to control the flow of urine in a patient, including implanting a plug device including an integral controller, a valve, and at least one sensor into the patient. An increase in an intravesicular pressure is sensed in at least one of the bladder and urethra, and a signal is supplied to the controller in response to the pressure increase. The valve is opened when the pressure reaches a first predetermined amount and closed when the pressure decreases to a second predetermined amount.

Still another embodiment relates to a method for controlling the urinary flow of a patient including positioning a valve in the patient in a location selected from the group of the urethra and the bladder. An electrical signal to a hydrogel component may actuate the valve and control the flow of urine.

Still another embodiment relates to a method for controlling the opening and closing of an implanted valve in a patient, including providing an implanted first control device in the patient to open and close the valve. A second control device is provided outside of the patient, and the first control device is programmed by sending a signal from the second control device to the first control device.

BRIEF DESCRIPTION OF THE DRAWINGS

Certain embodiments of the invention are described with reference to the accompanying drawings which, for illustrative purposes, are not necessarily drawn to scale.

FIGS. 5A and 5B illustrate hydrogel actuated operation of a planar helical sphincter according to an embodiment of the present invention, with 5A illustrating an open position and 5B illustrating a closed position.

FIGS. 6A and 6B illustrate a linear helical sphincter actuated by hydrogel fibers according to an embodiment of the present invention, with 6A illustrating an open position and 6B illustrating a closed position.

DETAILED DESCRIPTION

Certain embodiments of the present invention relate to a self-contained "intelligent" artificial urethral sphincter. In one preferred embodiment, the flow control apparatus is manufactured from a polyelectrolytic hydrogel and is controlled by an intravesicular pressure transducer. A plurality of materials and actuators may be used to achieve the actuation. Most episodes of involuntary loss of urine result from transient rises in intravesicular pressure (lasting less than one second). The artificial urethral sphincter will remain closed during these episodes, allowing the patient to remain continent. When the patient does desire to void, she need only strain in a manner which very closely mimics the natural physiology of micturition. Embodiments preferably use a sensor to monitor increase in the intravesicular pressure lasting over 1.5 seconds, and then trigger the sphincter to open, allowing free passage of urine. Alternatively, for older patients who are unable to strain effectively, the pressure sensor detects direct suprapubic pressure applied with one hand and subsequently trigger the urethral sphincter. Embodiments provide a non-surgical office based solution to the problem of stress incontinence, and could fundamentally and significantly alter the prevailing approach to the treatment of these patients.

Figure 1:
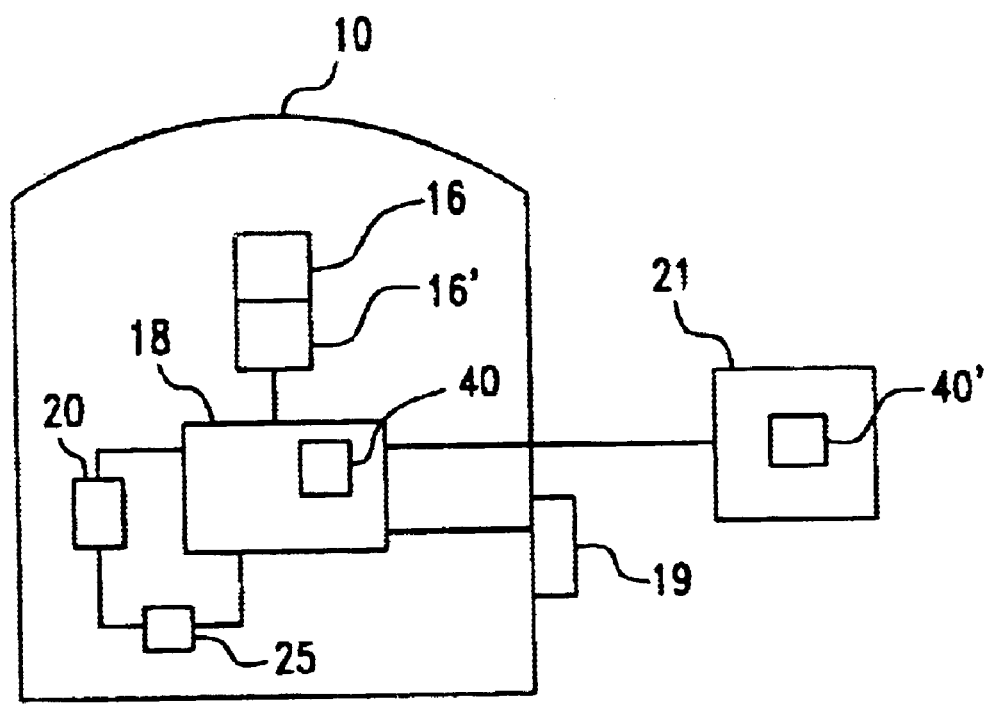
FIG. 1 is a schematic illustration of one embodiment of the present invention.
Figure 2A:
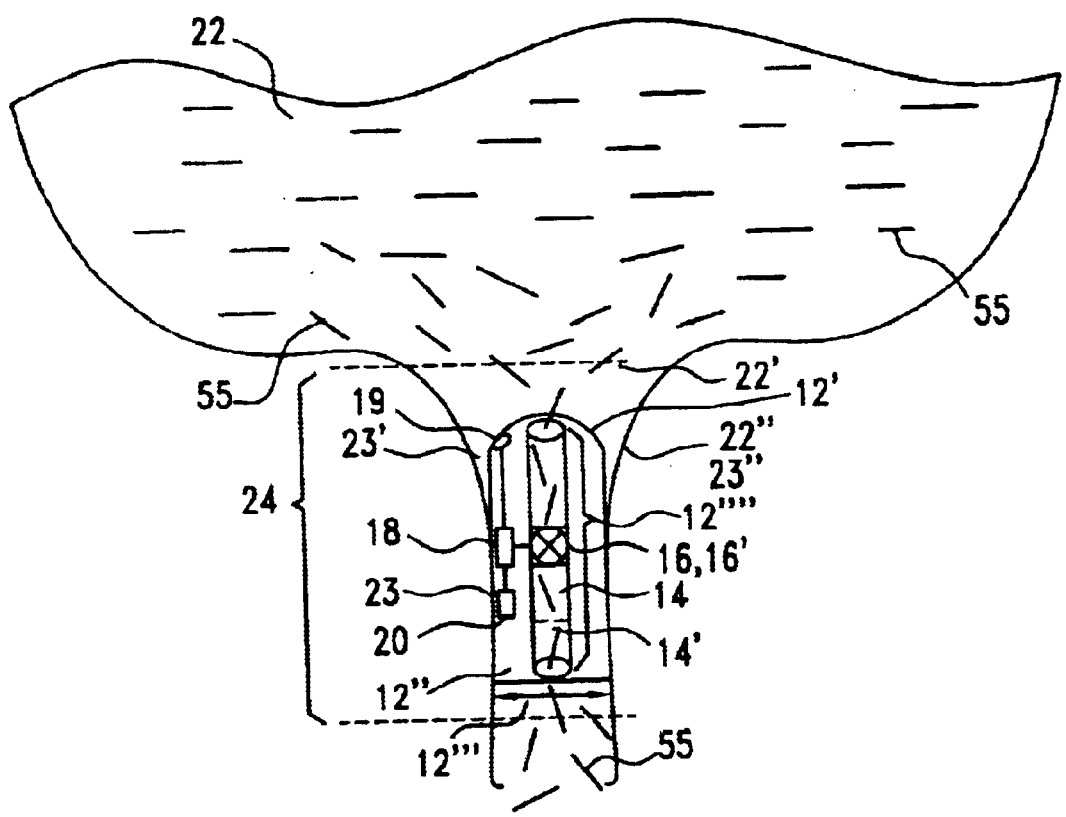
FIG. 2A is a lateral view illustrating an apparatus and the placement of the apparatus in the urinary tract according to an embodiment of the present invention.

Referring now to FIGS. 1 and 2A, one embodiment of an implanted plug apparatus 10 (also called plug 10) used to treat urinary incontinence comprises a plug member 12 with one or more lumens 14, a valve 16, an electronic control unit 18 (also called controller 18), at least one sensor 19 (which, if desired, may be located on the plug member 12) and an energy storage device 20. Valve 16 is preferably integral to or disposed over lumens 14. Valve 16 is preferably electronically coupled to electronic control unit 18. Electronic control unit 18 is also coupled (preferably via radiotelemetry or other electromagnetic communication means) to an external control unit 21 which is located outside the body. Plug 10 is designed to be implanted in the bladder 22 and/or urethra 23 at implant site 24 described herein, in order to regulate the flow of urine from bladder 22. In various other embodiments, plug 10 is adapted to be implanted anywhere in the gastrointestinal tract including, but not limited to, the pyloric valve and the anal sphincter to treat various diseases and pathologies associated with improperly functioning valves and/or sphincters.

Figure 2B:
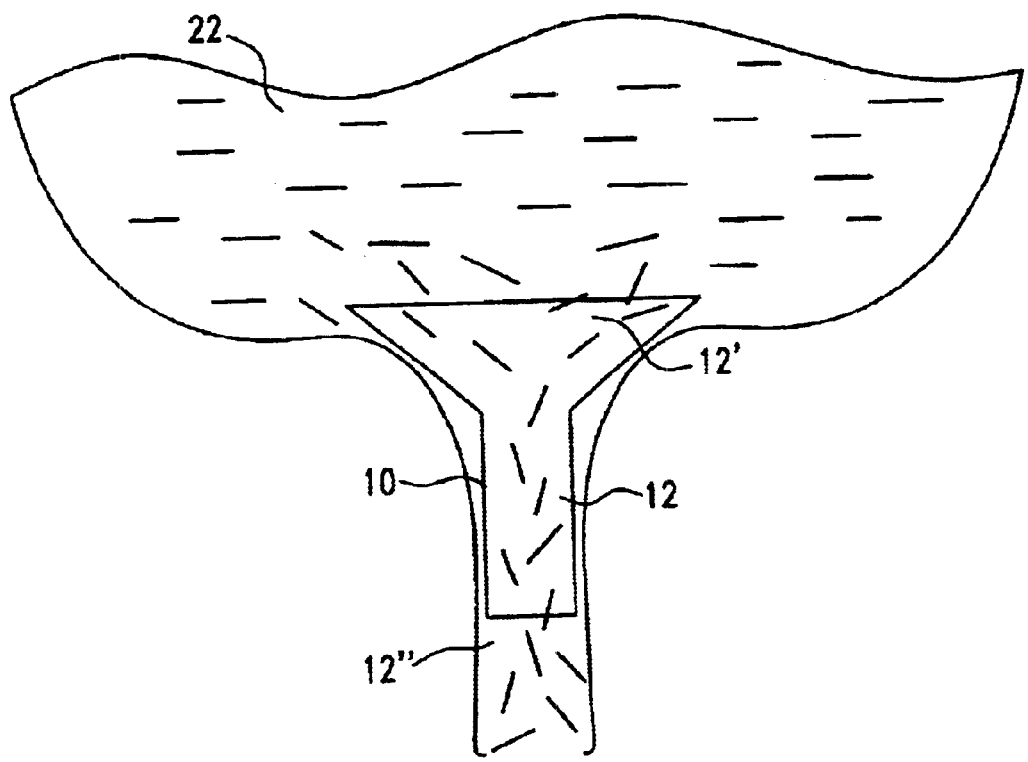
FIG. 2B is a lateral view illustrating an embodiment having a plug member with a conical section and a elongated cylindrical section.

Referring now to FIG. 2A, plug member 12 has a proximal portion 12' and distal portion 12" and is adapted to fit into the neck 22' of bladder 22 and/or upper (proximal) portions 23' of urethra 23 or portions of both but preferably extending no more than about one to about two centimeters into the urethra 23. This position as an implant location 24 for plug 10 reduces reduce the likelihood of a bladder or urinary tract infection. The plug body 12 may have a variety of shapes including, but not limited to, cylindrical, cone shaped, cork shaped, or a combination thereof. In one embodiment, as shown in FIG. 2B, plug member 12 comprises a conical proximal section 12' attached to a cylindrical distal section 12". Also, plug member 12 may be tapered over all or a portion of its length including but not limited to its proximal and distal portions 12' and 12". The taper can be straight or curved (such as concave and convex). In certain embodiments, the diameter of plug member 12 preferably range from about 0.2 to about 1.3 cm with more preferred embodiments of 0.6, 0.9 and 1.2 cm. The percent taper may preferably range from 0 to about 50% with preferred embodiments of about 10, 20, 30 and 40%. The diameter 12''' of at least a portion of the plug member 12 is preferably large enough to plug bladder neck 22' and/or urethra 23' and in certain embodiments can range from about 0.2 to 4 cm, with specific preferred embodiments of about 1, 2, 3 and 4 cm. Certain embodiments of the plug 12 are generally sized to fit within the urethra 23 and may also be sized to fit within at least a portion of the bladder 22 such as the bladder neck 22'. Also in various embodiments the length 12"" of plug member 12 can range from about 0.1 to 10 cm, with specific preferred embodiments of about 1, 2, 6, and 8 cm.

All or a portion of plug member 12 can be composed of a resilient material that may be compressed into a body lumen (such as the bladder neck or urethra) and subsequently expands back to fill and otherwise conforms interior 22" of bladder neck 22' and/or the interior 23" of urethra 23 to prevent the passage of any fluid through bladder neck 22' and or urethra 23. Suitable materials for plug member 12 include any number of elastomeric polymers including, but not limited to, silicone rubber, polyurethane and foams of either material using molding or multilumen extrusion technology and other polymer processing methods known in the art. Some other possible materials for plug member 12 include expanded PTFE and other hydrophobic microporous materials which block the flow of aqueous and other liquids but allow the passage of gas including water vapor. The use of such microporous materials provide a distinct technical advantage of preventing and/or reducing pressure differentials across plug member 12 which may unseat plug member 12 from its intended implant location 24, or otherwise compromise the fluid blocking integrity of the plug member 12.

Lumens 14 can extend all or a portion of the length of plug member 12. The diameter 14' preferably ranges from about 0.0002 cm to about 1.3 cm, with more specific embodiments of about 0.013, 0.025, 0.06, 0.13, 0.19, 0.25 and 0.6 cm. Embodiments with diameters smaller than about 0.002 cm may in certain embodiments be used to allow the passage of gas while blocking that of fluid due to surface tension properties. In certain embodiments the valve 16 can preferably be chosen from a variety of fluid valves including, but not limited to ball valves, needle valves, compression valves, pinch valves, solenoid valves, pressure differential valves, constriction valves and stop-cock valves. Valves 16 may be mechanically, pneumatically, or electromechanically actuated and may be actuated by an actuating device 16'. Additionally, valves 16 may be one way (bladder to urethra bias) or two-way. In certain embodiments valve 16 is designed to have an open fail safe position, e.g. it is designed to fail in the open position and the open position is the default position of valve 16. Also the flow aperture of valve 16 is preferably selectable in the continuous range from 0 to 100% open. Valve 16 can be constructed using a variety of methods such as molding, mechanical assembly and micromachining.

Figure 3:
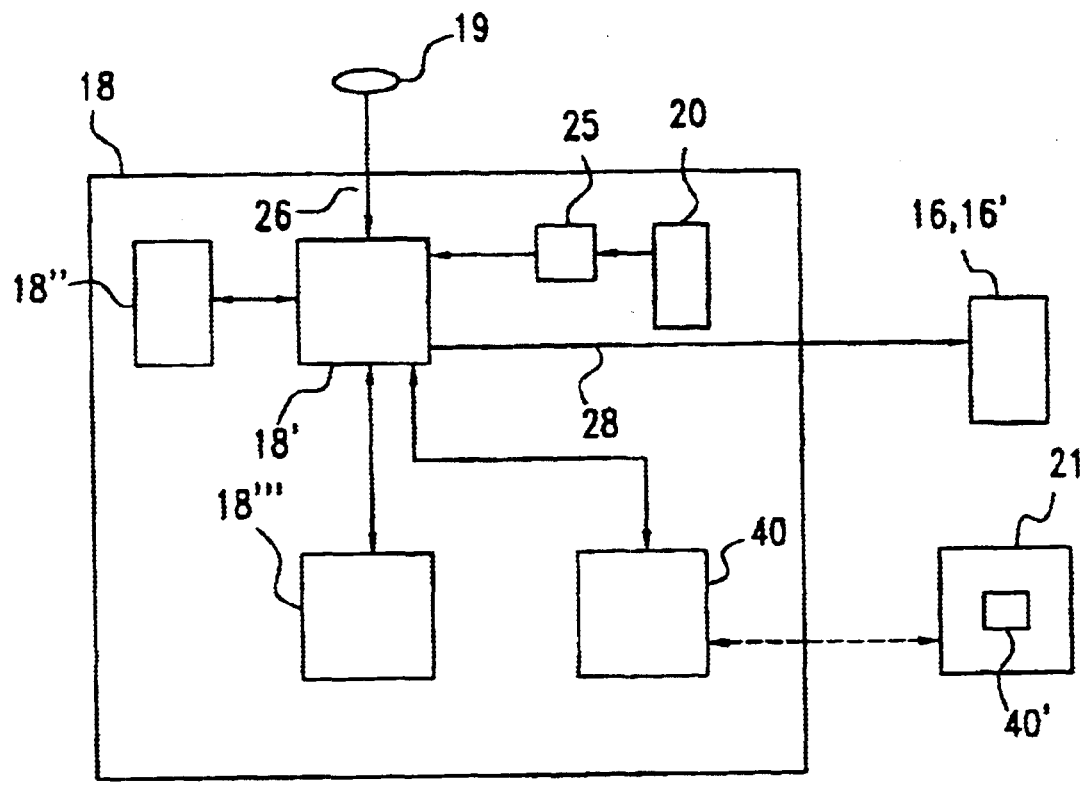
FIG. 3 is block diagram illustrating the finction of a controller according to an embodiment of the present invention.

Controller 18 provides the time interval and duration for the opening and closing of valve 16 as well as the amount of the opening of valve 16. Controller 18 may comprise an ASIC, custom designed very large scale integrated (VLSI) chip based microcontroller, or programmable microprocessor or microcontroller 18' such as any one of the CMOS low power microprocessors such as 80C85 from Intel, 6805 series microprocessor from Motorola, or a Stamp microprocessor from Parallex, Inc. As shown in FIG. 3, controller 18 may include an integral or connected ROM chip 18" for the storage of data and control algorithms (e.g. electronic instructions) and an integral or electrically connected timer chip 18'''. The controller 18 may receive electronic inputs 26 from sensors 19 and has electronic outputs 28 to valve 16 which cause the opening or closing of valve 16. The controller 18 may be electronically coupled to and powered by an energy storage device 20 which may be a battery 20.

The battery 20 may be rechargeable or single use. The controller 18 may also be preferably coupled to a transceiver device 40 for communication with external controller 21 as will be discussed herein.

Chemistries for battery 20 may include, but are not limited to, lithium, lithium ion, lithium polymer, nickel-cadmium, and nickel-metal hydride. The voltage of battery 20 may be measured using a voltage comparator 25 or other voltage sensing circuit 25 that is integral or otherwise electrically coupled to controller 18 and battery 20.

Sensors 19 include, but are not limited to: strain gauge pressure sensors for sensing bladder and urine hydrostatic pressure; pH sensors for sensing urine pH; LEDs and photomutlipliers for sensing urine optical density and/or concentration; chemical FETs for sensing pH, ammonia ion glucose and other chemical concentrations; Clarke electrodes for sensing dissolved oxygen concentrations; flow sensors such as ultrasound, electromagnetic or anemometric sensors (thin film) for sensing both urine flow rates and volumes; and optical, electrical resistance or LVDT sensors for sensing bladder wall tension and displacement.

Under normal conditions the valve 16 is maintained by the controller 18 in a closed position. The controller 18 may preferably be programmed by the patient to sufficiently open valve 1C to allow the passage of urine 55 under three modes of operation: i) a time mode, where valve 16 opens at preset time intervals programmed into controller 18, where the time intervals may include periods from about 0.1 to about 8 hours with preferred intervals of about 0.5, 1, 2, 3 and 4 hours; ii) sensor mode, where input from sensors 19 relating to the volume, pressure or physical properties (e.g chemical content) of urine in the bladder causes valve 16 to open; and, iii) manual mode, where the user manually causes valve 16 to open based on user input to external controller 21. Controller 18 may be used to alert the patient of an impending valve opening, over a range of user selected alert times, preferably in the range of about 1 to 30 minutes, with preferred alert times of about 5, 10, 15 and 20 minutes. Alerts may be in the form of an audible sound such as a beep or a vibration (produced by components/devices described herein) and may be selected by the patient using external controller 21. In certain embodiments, controller 18 may open valve 16 for a fixed time (e.g., about 0.1 to about 5 minutes, with preferred embodiments of 0.5, 1 and 2.5 minutes) or in an alternative embodiment, may control the opening of valve 16 based on feedback control using input parameters such as bladder pressure, bladder wall tension, urine flow rate, and/or total volume of urine voided, which may all be derived or calculated based on inputs 26 from sensors 19. As a safety precaution to prevent hydronephrosis, hydroureter or other distention of bladder 22 or urethra 23, controller 18 may be programmed to open valve 16 at a preset time from the last void (e.g. 1 to 4 hours) which would repeat at set intervals (e.g. 1 to 4 hours) should any of the following conditions occur: i) the user does not input a void time interval or other sensor mode or otherwise does not void within a preset time; ii) a communications break occurs between controller 18 and external controller 21, iii) a malfunction occurs in valve actuator 16', sensors 19, controller 18 or energy storage device 20 (e.g., low or dead battery which would be detected via the use of voltage comparator 23).

Figure 4:
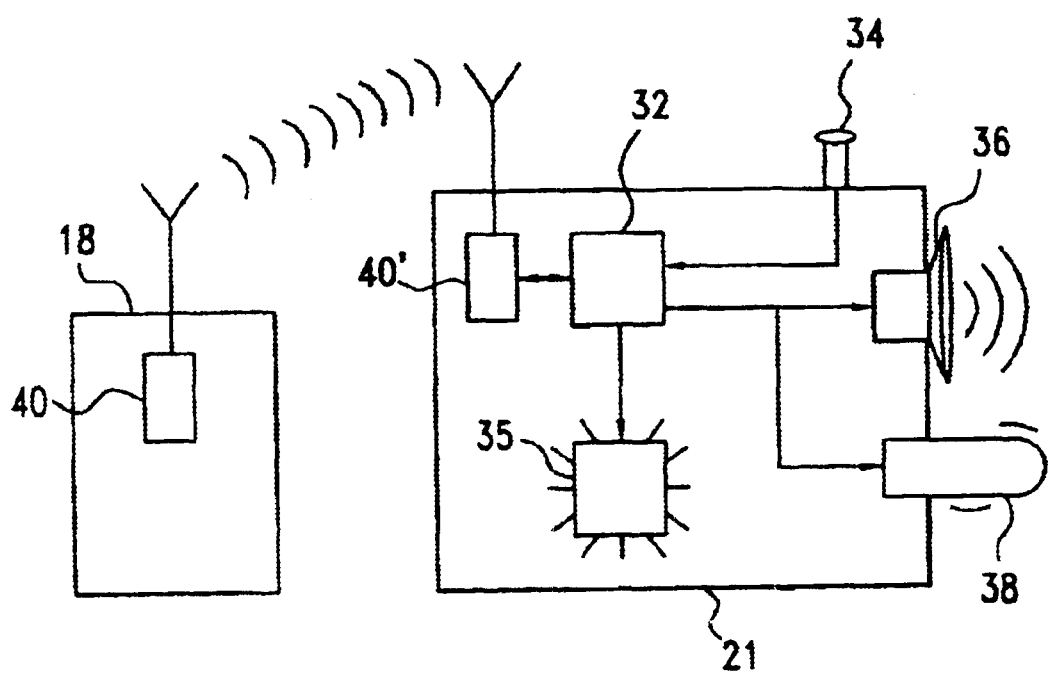
FIG. 4 is a block diagram illustrating the function of the external controller.

In certain embodiments external controller 21 may comprise a wristwatch device or belt-worn device similar in size and shape to a pocket beeper. Referring now to FIG. 4, the external controller may preferably include a microprocessor 32, one or more buttons 34, a display 35 (including, but not limited to an LED display), an audible alarm 36 (such as a speaker), a vibration device 38, and a radio frequency transceiver 40'. Buttons 34 allow the patient to input various settings and values into microprocessor 32 for communication to controller 18 via transceiver 40. Such inputted values may include alert times and void time intervals which may be stored in a memory register of microprocessor 32. Buttons 34 may also allow the user to override a preprogrammed void or to initiate a manual void in a selectable amount of time. Additionally, buttons 34 may allow the user to reprogram the clock time maintained by controller 18. Controller 18 and external controller 21 may preferably communicate via transceivers 40 and 40' via radio frequency (or other electromagnetic medium) at preset regular intervals. Controller 18 may inform external controller 21 of its functional status, as well as other information such as next void time and current void program mode (e.g. time or bladder pressure). Controller 18 may also alert external controller 21 of any malfunction of plug device 10, which may cause audible alarm 36 to sound and/or vibration device 38 to go off, and may cause the display of the malfunction to appear on display 35.

Certain preferred embodiments are constructed from "biomimetic" materials. Biomimetic materials are a class of materials that utilize biologically inspired, biologically compatible materials that are capable of existing within the human body's hostile environment. The environment imposes significant restrictions in terms of size, temperature, pH, power limitations, and biocompatibility. A plurality of mechanisms, including, but not limited to mechanisms such as electromechanical valves, a piezo-electric actuators, shape memory alloy valves and actuators, and hydrogels may be used in certain embodiments.

In one embodiment, an electromechanical mechanism for a valve or a sphincter is designed from metallic parts and actuated by electromagnetic, pneumatic or hydraulic forces. The valve may reside inside the urinary tract and under the aforementioned actuation mechanisms, the valve may be opened or closed. The valve may then permit the flow of urine from the bladder down the urinary tract. The dimensions of the valve may conform to the size of the urinary tract. A preferred location of the valve would be at the interface of the bladder and urethra. Other preferred locations are down the urethral vessel.

In yet another embodiment, a piezo-electric actuator is used to create movement of the valve or the sphincter using crystals such as PZT. An advantage of such an actuator is that the power consumption is low and transduction efficiency is high. The crystal is driven by a high voltage source. Preferred locations are again at the interface of the bladder and urethra, and down the urethral vessel.

In yet another embodiment, shape memory alloys (SMA) such as Nitinol (alloy of Nickel and Titanium) are used. The SMA have the property that when heated, they hold one set of stress-strain relationship (modulus of elasticity), and when cooled, another one. In a preferred design of the device, a single or multiple strand of SMA wires is coiled to form a spring shaped valve design. In effect, the heated SMA would coil or constrict and a cooled one would uncoil or open up. An advantage is the enormous forces that can be produced by this actuator and its composition would make it very durable and reliable. In yet another design, two sets of wires working as agonist and antagonist are used to open and close the orifice by the relative strength of the opposing actions of these actuators.

Hydrogels are a class of polymers that form gel like substances from constituent polymer matrix. The hydrogel matrix is capable of changing its shape in response to stimuli such as changes in pH, use of different fluids such as acetone, ionic concentrations, and passage of electrical current. A unique property of hydrogels is a muscle like property of expanding and contracting and producing force. In the design of urinary catheter and actuator/valve, the hydrogel materials offer many benefits, including: biocompatibility, low power, biomimetic muscle like actuation. The ionic concentrations or pH of the fluids, and the actuation command such as the fluid used, its pH or the electrical current, determine the hydrogel properties.

In one embodiment, the hydrogel is actuated under voluntary action, under electrical field action. Preferably, a hydrogel known as a polyelectrolytic gel, is used. Application of an electrical field affects the properties of the polyelectrolytic gel, causing it to shrink or swell, stretch or contract, and by that action, carry load. Preferred materials are polyvinyl alcohol (PVA) with an average molecular weight of about 100,000 and polyacrylic acid (PAA) with a molecular weight of about 500,000 to 1,000,000. These polymeric gels produce tangled network when immersed in a liquid medium and they are neither wholly solid nor liquid. Different formulation of the hydrogels, including, but not limited to mainly strands, stand bundles, strips and tubings, may be used. Polyelectrolytic hydrogels (p-gels) offer the possibility of controlling the gel mechanics via external chemical or electrical means. The p-gels contain ionizable, redox or photoactive functional group. Ion exchange initiated chemically or electrically results in reversible swelling of the gel. The gel typically contains a cross-linked network of polymer chain, salt, counter ions and solvent. The gel swells or changes shape when under changes in ionization conditions, the molecular chain shows shape change (e.g., from long active strand to highly coiled network). Dissociation and re-association of ionizable groups to the polymer causes modulation of polymer chain conformation because of electrostatic interactions. It should be noted that polyelectrolytic gels generally need an electrolytic or solvent bath for operation. Use of gel in the bladder or urethra may be feasible, but preferably, the gel fibers along with the electrolyte reside within the annulus of the double walled urethral tubing so that contact with body fluids is minimized and biocompatibility and infection/contamination are reduced or eliminated.

A preferred mode of operation of the polyelectrolytic gel is in electrolytic solution at optimized pH levels. In the optimized electrolytic medium, the performance of the gel can be optimal and the gel does not need to contact urine. However, placing the gel sphincter or valve directly inside the urine offers some benefits of not needing additional reservoir of solvent/electrolyte and the ionic and pH conditions of the urine can also be utilized to automatically control the properties of the gel.

In another aspect of certain embodiments, fibers and fiber bundles may be used to obtain certain advantages. A large number of thin tensile elements may provide greater strength (in a manner analogous to a rope made of multiple fibers tightly woven together). Weakening or breakage of individual hydrogel fibers should not have a significant deleterious effects and also variations in their composition or actuation parameters will not have a significant deleterious effect, since the composite performance would matter in operating the sphincter. The strength, speed and other parameters may be controlled by electrical fields, electrochemical diffusion, solution surrounding the gel, and the mechanics of the fibers and fiber composite.

A description of a preferred embodiment of a hydrogel-based sphincter valve design follows. The valve comprises a mechanism that is made up of an actuator material shaped like a helix that coils around the urethral tubing. When activated, the helix contracts, similar to the coiling of a spring or a DNA molecule. As the helix coils, it constricts the urethral tubing, creating a sphincter. Release of the actuation uncoils the spring and opens the sphincter. The helical actuator preferably only contacts the silicone or polyurethane tubing and not the body fluids or body environment. The helical valve is small because it is essentially formed as a spring or coiled strand, loosely wrapped around the urethral tubing. In one preferred design, a sphincter using a bundle of muscle fibers is wrapped around a silicon tubing. The hydrogel fibers are actuated by the application of electrical field. The design preferably accommodates the full hydrogel muscle (made from many muscle fibers) in a very limited space (such as less than about 0.6 cm diameter) through the use of a helical sphincter.

In one preferred embodiment, the sphincter valve 50 is mounted at the juncture of the bladder and the urethra. The sphincter 50 as illustrated in FIG. 5 is made from two annular rings: an inner ring 42 with a diameter of preferably about 0.25 cm and the outer ring 43 with a diameter of preferably about 0.5 cm. Hydrogel strips, wires, or fibers 44, 45, 46, 47 of preferably about 0.025 cm diameter or smaller and a length of preferably about 0.25 to about 5 cm are mounted between the inner ring 42 and the outer annular ring 43, preferably, however, at a stagger (preferably about 45 to 90 degree stagger between the inner and the outer annulus). As illustrated in FIG. 5A under normal conditions (without current), the sphincter remains open and allows passage of urine. As the fibers 44–47 are actuated by application of electrical current between the outer and the inner annulus, the fibers contract as illustrated in FIG. 5B. Because of the stagger, these fibers rotate the inner ring 42 with respect to the outer ring 43 as the fibers contract and thus open the sphincters. This mechanism can be seen as something analogous to an iris of a camera (the shutter that opens and closes to allow light to reach the film). The sphincter may preferably be made of an outer tubing and an inner, softer tubing. The actual number of strands or fibers 44–47 may be significantly greater than 4, and may cover the whole inner annulus. The closed sphincter will have stiffer, shorter hydrogel strands; electrical activation results in softening and lengthening, leading to opening of the inner tube and urine voiding.

In yet another embodiment of a helical sphincter, a linear helical sphincter is utilized. This embodiment is designed in view of the limited space within which to mount the hydrogel fibers. Since in general one is limited to a uretheral catheter of the size of about 0.5 cm diameter, it may be difficult to mount annular sphincters or valves. The embodiment illustrated in FIG. 6 utilizes construction of a linear sphincter 52 made from a long strand of fiber (one or more fibers) 51 wrapped helically onto the inner tubing 48, between the inner tubing 48 and the outer tubing 49, running from the bladder orifice to at least about 2.5 cm and up to 5 cm down. Essentially, the fiber 51 wraps around the inner tubing 48 throughout the length of the urethral tube. The sphincter works, as illustrated in FIG. 6(b) by tightly coiling the fiber 51 around the inner tubing 48 and constricting it, thus impeding the flow of urine. The fiber action is initiated by the application of an electrical field. When the electric field is applied, the fibers constrict and thus tighten their noose around the inner tubing and forcing it to close and block the passage of urine. Because the fibers can be run along the length of the tubing, a thin fiber strand, like a thin rope, may be more readily placed inside the small catheter.

The action of the linear sphincter may be considered to be analogous to wringing a towel or twisting a rope. The aforementioned embodiment provides a fail-safe mechanism of keeping the sphincter open in absence of power application and thus allowing the passage of urine. Because the action of the hydrogel constriction takes place throughout the length of the prosthesis, this embodiment is expected to result in a better distribution of fiber forces and a more complete closure of the sphincter. Note that the hydrogel may never contact urine and resides in the annulus, and may be bathed in saline or an equivalent electrolyte. The electric field may be applied between the top and the bottom of the tubing.

While the designs described in aforementioned figures represents certain preferred embodiments, other embodiments are also envisaged. In another embodiment, the fibers constrict the sphincter under normal, unpowered condition existing in absence of applied electric field. Thus, no urine is allowed to flow. When the field is applied, the fibers open the sphincter, and allow flow of urine. This design has the benefit that electric power is used only when the sphincter is opened when urine flow is desired.

In addition, certain embodiments are applicable to uses other than regulating the flow of urine. For example, embodiments may include devices and methods for controlling anal incontinence. Embodiments may also be applied to other locations in the body to regulate the flow of a substance in the body. For example, an embodiment located in the vicinity of the stomach along the digestive tract may find application in dieting or in otherwise controlling the amount and/or rate of digestion of food by regulating its flow.

While the invention described above presents some of the preferred embodiments, it is to be understood that the invention in not limited to the disclosed embodiment but rather covers various modifications and equivalent arrangements included within the spirit and scope of the appended claims.

What is claimed is:

1. An apparatus comprising:
   a plug member including a lumen therein;
   a valve adapted to open and close the lumen in response to a control signal;
   a controller adapted to transmit a control signal to the valve; and
   at least one sensor adapted to send a sensor signal to the controller;
   wherein the plug member is adapted to be positioned entirely within a patient's body, and wherein any part of the apparatus that is physically coupled to the plug member is adapted to be positioned entirely within the patient's body.

2. An apparatus as in claim 1, wherein the valve and controller are positioned within the plug member.

3. An apparatus as in claim 2, wherein the at least one sensor is positioned in or on the plug member.

4. An apparatus as in claim 1, further comprising an energy storage device electrically coupled to the controller.

5. An apparatus as in claim 1, wherein at least part of the apparatus comprises a polyelectrolytic hydrogel.

6. An apparatus as in claim 5, wherein the plug member is configured to fit into at least one location selected from the group consisting of the bladder and the urethra.

7. An apparatus as in claim 1, wherein the plug member includes a tapered portion.

8. An apparatus as in claim 1, wherein the plug member comprises a shape selected from the group consisting of cylindrical, conical, and combinations of cylindrical and conical.

9. An apparatus as in claim 1, wherein the plug member comprises a resilient material.

10. An apparatus as in claim 1, wherein the plug member comprises a hydrophobic micoporous material.

11. An apparatus as in claim 1, wherein the valve is a one way valve.

12. An apparatus as in claim 1, wherein the valve is a two-way valve.

13. An apparatus as in claim 1, wherein the valve includes a piezoelectric actuator.

14. An apparatus as in claim 1, wherein the valve includes a shape memory alloy.

15. An apparatus as in claim 1, wherein the valve includes a hydrogel polymer.

16. An apparatus as in claim 1, wherein the controller comprises an electronic controller selected from the group consisting of an ASIC and a programmable microprocessor.

17. An apparatus as in claim 1, wherein the controller is programmable to open the valve to permit the flow of urine under at least one mode of operation selected from the group consisting of a predetermined time interval operation, a sensor operation, and a manual actuation operation.

18. An apparatus as in claim 1, wherein the controller is programmable to operate under a time interval mode, a sensor mode, and a manual mode.

19. The apparatus of claim 1, further comprising an external device comprising at least one of a second controller, a receiver, and a signal generator.

20. The apparatus of claim 19, wherein the external device comprises a microprocessor, a transceiver, an input mechanism.

21. The apparatus of claim 20, wherein the external device comprises at least one of a display, an alarm, and a vibrator.

22. The apparatus of claim 1, further comprising an external control device adapted to program the controller, the external control device adapted for use outside of the patient's body.

23. An apparatus as in claim 1, wherein the sensor is coupled in direct physical contact with the plug.

24. An apparatus as in claim 1, wherein the controller is electrically connected to the valve.

25. An apparatus as in claim 1, wherein at least a portion of the plug member comprises at least one shape selected from the group consisting of cylindrical and conical.

26. A flow control apparatus comprising an assembly for insertion into a patient's body, the assembly adapted to be positioned so that no portion of the assembly and no portion of the flow control apparatus that is physically coupled to the assembly is located outside of the patient's body, the assembly comprising:
   an intravesicular pressure transducer; and
   a polyelectrolytic hydrogel coupled to the transducer, the polyelectrolytic hydrogel being adapted to receive a signal from the intravesicular pressure transducer and to control flow in response to the signal.

27. An apparatus for controlling the flow of a substance in a patient's body, comprising:
   an implantable valve adapted to be positioned along a route that the substance flows through the body;
   an implantable controller for opening and closing the valve in response to an input provided by the patient; and
   an implantable sensor which signals the controller to open the valve in response to the input provided by the patient;
   wherein the implantable valve, the implantable controller, the implantable sensor, and any additional components physically coupled to at least one of the implantable valve, the implantable controller and the implantable sensor are adapted to be positioned entirely within the patient's body.

28. An apparatus as in claim 27, wherein the input provided by the patent is selected from the group consisting of a pressure signal and a timed signal.

29. An apparatus as in claim 27, further comprising an external control device for sending a signal to the sensor from a position outside of the patient's body.

30. A method to control the flow of urine in a patient, comprising:
   implanting a plug device including an integral controller, a valve, and at least one sensor into the patient so that the plug device and any components physically coupled to the plug device are positioned entirely within the patient;
   sensing an increase in an intravesicular pressure in at least one of the bladder and urethra and supplying a signal to the controller in response to the pressure increase;
   opening the valve when the pressure reaches a first predetermined amount; and
   closing the valve when the pressure decreases to a second predetermined amount.

31. A method as in claim 30, further comprising applying suprapubic pressure to supply a signal to the controller.

32. A method as in claim 30, wherein the valve is formed from a material selected from the group consisting of a shape memory alloy and a hydrogel polymer.

33. A method for controlling the urinary flow of a patient, comprising:
   positioning a valve and a lumen in the patient in a location selected from the group of the urethra and the bladder so that the valve and lumen and any components physically coupled to the valve and lumen are positioned entirely within the location selected from the group of the urethra and the bladder;
   positioning a sensor in the patient in a location selected from the group consisting of the urethra and the bladder;
   sensing a condition in the patient relating to the urinary flow using the sensor; and
   applying an electrical signal to actuate the valve and control the urinary flow through the lumen.

34. An apparatus to regulate urine flow, comprising:
   a valve adapted to open and close in response to a signal to regulate urine flow;
   at least one sensor; and
   a controller adapted to control the valve;
   wherein the valve, sensor, controller and any component physically coupled to at least one of the valve, sensor and controller is adapted to fit entirely inside of at least one of the bladder and the urethra.

35. A flow control apparatus for insertion into a patient's body, comprising:
   an intravesicular pressure transducer coupled to a controller;
   the controller adapted to receive a transducer signal from the intravesicular pressure transducer; and
   a polyelectrolytic hydrogel electrically coupled to the controller, the polyelectrolytic hydrogel being adapted to receive an electric field signal from the controller, wherein the polyelectrolytic hydrogel is further adapted to control flow be undergoing a change in dimension in response to the electric field signal;
   wherein the flow control apparatus is adapted to be entirely positioned within the patient's body.

36. An apparatus comprising:
   a plug member including a lumen;
   a valve positioned within the plug member and adapted to open and close the lumen in response to a control signal;
   a sensor adapted to transmit a sensor signal; and
   a controller positioned within the plug member and adapted to receive the sensor signal, the controller also adapted to control the valve in response to the sensor signal;
   wherein the sensor is electrically connected to the controller member and
   wherein the plug member is adapted to be positioned entirely within a patient's body and any part of the apparatus that is physically coupled to the plug member is adapted to be positioned entirely within the patient's body.

37. An apparatus for controlling the flow of urine in a patient, comprising:
   implantable means for housing a lumen;
   implantable valve means for opening and closing the lumen;
   implantable means for sensing a condition related to the flow of urine inside the patient; and
   implantable means for controlling the valve means in response to a signal from the sensing means;
   wherein any part of the apparatus that is physically coupled to the implantable means for housing a lumen is adapted to be positioned entirely within the patient.

38. An apparatus for controlling the flow of urine in a patient, comprising:
   a plug member including a lumen therein;
   a valve adapted to open and close the lumen in response to a control signal;
   at least one sensor adapted to sense a condition in the patient and provide an output; and
   a controller adapted to transmit a control signal to the valve based on the output from the sensor;
   wherein the plug member, the valve, the sensor and the controller are positioned entirely within the patient, and wherein any part of the apparatus that is physically coupled to the plug member is adapted to be positioned entirely within the patient.

39. An apparatus as in claim 38, wherein the output from the sensor relates to at least one condition in the patient selected from the group consisting of bladder pressure, bladder wall tension, urine flow rate, and volume of urine voided.

40. An apparatus as in claim 38, wherein the at least one sensor comprises at least one sensor selected from the group consisting of: (1) strain gauge pressure sensors adapted to sense bladder and/or urine hydrostatic pressure; (2) pH sensors adapted to sense urine pH; (3) LEDs and/or photomutlipliers adapted to sense urine optical density and/or concentration; (4) chemical field effect transistors adapted to sense at least one of pH, ammonia ion glucose and other chemical concentrations; (5) electrodes for sensing dissolved oxygen concentrations; (6) flow sensors including at least one selected from the group of ultrasound, electromagnetic and anemometric sensors adapted to sense urine flow rates and/or volumes; and (7) at least one selected from the group of optical, electrical resistance and LVDT sensors adapted to sense bladder wall tension and/or displacement.

41. An apparatus as in claim 38, wherein the valve includes a default position that configures the valve to be in an open position.

* * * * *